(12) United States Patent
Walsh et al.

(10) Patent No.: US 6,908,627 B2
(45) Date of Patent: Jun. 21, 2005

(54) CONDITIONED MEDIA FOR INHIBITING GROWTH OF TUMOR CELLS

(75) Inventors: Catherine Walsh, Sarasota, FL (US); Carl Luer, Sarasota, FL (US)

(73) Assignee: Mote Marine Laboratory, Sarasota, FL (US)

( * ) Notice: Subject to any disclaimer, the term of this patent is extended or adjusted under 35 U.S.C. 154(b) by 419 days.

(21) Appl. No.: 10/173,211

(22) Filed: Jun. 14, 2002

(65) Prior Publication Data

US 2002/0197329 A1 Dec. 26, 2002

Related U.S. Application Data

(60) Provisional application No. 60/300,556, filed on Jun. 21, 2001.

(51) Int. Cl.[7] .............................................. A61K 35/60
(52) U.S. Cl. ...................................................... 424/559
(58) Field of Search ......................................... 424/559

(56) References Cited

U.S. PATENT DOCUMENTS

| 5,075,112 A | 12/1991 | Lane |
| 5,192,756 A | 3/1993 | Zasloff et al. |
| 5,985,839 A | 11/1999 | Dupont et al. |

OTHER PUBLICATIONS

Piferrer, F.C. and Callard, G. V., Inhibition of Deoxy ribonucleic Acid Synthesis During Premeiotic Stages of Spermatogenesis by a Factor from Testis–Associated Lymphomyeloid Tissue in the Dogfish Shark, Biology of Reproduction, 1995, pp. 390–398, vol. 53, Society for the Study of Reproduction, Madison, WI, United States.

Walsh, C.J. and Luer, C.A., Comparative Phagocytic and Pinocytic Activities of Leucocytes from Peripheral Blood and Lymphomyeloid Tissues of the Nurse Shark and Clear nose Skate, Fish & Shellfish Immunology, 1998, pp. 1998, pp. 197–215, vol. 8, Academic Press, United States.

Luer, C. A, Walsh, C.J., Bodine, A.B., Wyffels, J.T., Scott, T.R., The Elasmobranch Thymus: Anatomical, Histological, and Preliminary Functional Characterization, The Journal of Experimental Zoology, 1995, pp. 342–354, vol. 273, Wiley–Liss, United States.

McKinney, E.C., Shark Lymphocytes: Primitive Antigen Reactive Cells, Annual Review of Fish Diseases, 1992, pp. 43–51, vol. 2, Pergamon Press, United States.

Fänge, R., and Mattison, A., The Lymphomyeloid (Hemopoiette) System of the Atlantic Nurse Shark, *Ginglymostoma Cirratum*, Biol. Bull., 1981 pp. 240–249, vol. 160, The Marine Biological Laboratory, United States.

Lloyd–Evans, P., Development of the Lymphomyeloid System in the Dogfish, *Scyliorhinus Canicula*, Developmental and Comparative Immunology, 1993, pp. 501–514, vol. 17, Pergaon Press, United States.

Fänge, R., and Pulsford, A., Structural Studies on Lymphomyeloid Tissues of the Dogfish, Scyliorhimus L., Cell and Tissue Research, 1983, pp. 337–351, vol. 230, Springer–Verlag, Germany.

Lee A. and Langer, R., Shark Cartilage Contains Inhibitors of Tumor Angiogenesis, Science, 1983, pp. 1185–1189, vol. 221, American Association for the Advancement of Science, United States.

Folkman, J. and Klagsbrun, M., Angiogenic Factors, Sciences 1987, pp. 442–447, vol. 235, American Association for the Advancement of Science, United States.

*Primary Examiner*—Jean C. Witz
(74) *Attorney, Agent, or Firm*—Catherine J Walsh; Cecilia A Walsh

(57) ABSTRACT

Conditioned media compositions having valuable biological activity are obtained from cultures of immune cells from elasmobranch fishes. Methods are provided for producing the conditioned media compositions. Conditioned media obtained using epigonal cells from bonnethead sharks (*Sphyrna tiburo*) and lemon sharks (*Negaprion brevirostris*) demonstrate strong anti-tumor activities. The conditioned media compositions can be used for treating tumor proliferation and in immunosuppressive therapy.

31 Claims, 7 Drawing Sheets

Effect of Lemon Shark Epigonal CM on Growth of WEHI 164 Cells

CONDITIONED MEDIA FOR INHIBITING GROWTH OF TUMOR CELLS

CROSS REFERENCE TO RELATED APPLICATION

This application claims priority from Provisional Application Ser. No. 60/300,556, filed Jun. 21, 2001, entitled "Conditioned Media from Elasmobranchs to Inhibit Growth of Tumor Cell Lines," the disclosure of which is incorporated herein by reference.

FIELD OF THE INVENTION

This invention relates to conditioned media compositions made from immune cells from elasmobranch fishes, to methods of making such compositions, to anti-tumor and immunosuppressive compounds comprising such compositions, and to anti-tumor and immunosuppressive treatment methods comprising such compositions.

BACKGROUND OF THE INVENTION

Elasmobranch fishes (sharks, skates, and rays) are relatively disease free (Wellings, S. R., 1969, Natl. Cancer Inst. Mongr. 31:59–128), particularly with regard to the lack of cancerous tumors. As documented by the Registry of Tumors in Lower Animals maintained at the Smithsonian Institution (Harshbarger, J. C., 1965-present), a few tumors have been described from this large subclass of fish, but their incidence is acknowledged to be a rarity. Since elasmobranchs are notably resistant to tumor development, these fish have been well studied with regard to their cancer resistance. The immune system in elasmobranchs has been studied to investigate anti-tumor and cytokine-like factors present in their immune systems. Compared to other lower vertebrate animal systems, relatively little functional information is available regarding the cells and tissues which comprise the elasmobranch immune system (McKinney, E. C., 1992, Ann. Rev. of Fish Diseases 2:43–51). While elasmobranchs do not have bone marrow, they do have a thymus (Fänge, R. and Pulsford, A., 1983, Cell and Tissue Research 230:337–351; Lloyd-Evans, P., 1993, Developmental and Comparative Immunology 17:501–514; Luer, C. A., Walsh, C. J., Bodine, A. B., Wyffels, J. T., Scott, T. R., 1995, J. of Experimental Zoology 273:342–354) and a spleen, as well as two lymphomyeloid organs which are unique to this subclass of fish, the Leydig organ surrounding the esophagus, and the epigonal organ associated with the gonads. Histologically, the Leydig and epigonal organs of elasmobranchs resemble bone marrow and lymph nodes of higher vertebrates and are very active in granulopoiesis and lymphocyte production (Fänge, R. and Mattison, A., 1981, Biol. Bull. 160:240–249; Fänge, R., 1987, Arch. Biol. 98:187:208; Fänge, R., 1994, Fish and Shellfish Immunology 4(6):405:411). While many elasmobranchs possess both of these lymphoid organs, some have only the epigonal organ (Honma, Y., Okabe, K., and Chiba, A., 1984, Jap. J. Icht., 31:47–54; Fänge, 1987). Other than the role of these tissues in granulopoiesis and lymphopoiesis, little is known of the functional aspects of the cells within these unique tissues. Cells produced by the epigonal and/or Leydig organs may be important in immune responses and in inflammatory processes of elasmobranchs (Fänge and Mattisson, 1981).

Shark cartilage has been studied with regard to its anti-angiogenic properties. Lee and Langer (1983, Science 221:1185–1187) and Folkman and Klagsbrun (1987, Science 235:442–446) have shown that sharks produce a substance which inhibits neovascularization. There are several therapeutically valuable compounds isolated from sharks. For example, U.S. Pat. No. 5,192,756 discloses a compound having antibiotic and antiprotozoal properties isolated from the stomach of a dogfish shark. U.S. Pat. No. 5,075,112 describes a method for inhibiting angiogenesis using shark cartilage, and U.S. Pat. No. 5,985,839 describes extracts of shark cartilage having anti-angiogenesis properties and an inhibitory effect on cell tumor lines.

An antimitogenic factor derived from the epigonal organ of a dogfish shark was shown to reversibly inhibit DNA synthesis in spermatocysts in the testis (Piferrer, F. C., and Callard, G. V., 1995, Biology of Reproduction, 53:390–398). Previously, juvenile (total length<75 cm) nurse shark (*Ginglymostoma cirratum*) epigonal cells and cleamose skate (*Raja eglanteria*) epigonal and Leydig organ cells were placed into short-term culture (Walsh, C. J. and Luer, C. A., 1998, Fish and Shellfish Immunology, 8:197–215). These cultures included a cell culture medium that had been modified to approximate the normal osmolarity (970 mOsm) of elasmobranch cells using urea, NaCl, and trimethylamine N-oxide (TMAO) to balance the medium isotonically. Urea is a major balancing osmolyte naturally present in marine cartilaginous fish, including elasmobranch fishes. TMAO is a solute naturally concentrated in the urea-rich cells of elasmobranchs that serves to offset the damaging effects of urea on intracellular protein structure and function by raising the free energy of the denatured state of proteins, and also stabilizes the osmolyte urea. These preparations were not evaluated for anti-tumor or immunosuppressive activity. Therapeutically valuable biological activity demonstrated by a factor isolated from cultures of immune cells of elasmobranchs has not yet been described.

SUMMARY OF THE INVENTION

The present invention provides compositions having therapeutically valuable biological activities obtained from cultures of immune cells from elasmobranch fishes (especially sharks from the order Carcharhiniformes), to methods for producing these compositions, to anti-tumor compounds and immunosuppressive compounds comprising these compositions, and to anti-tumor and immunosuppressive treatment methods comprising these compositions. The compositions are prepared from cell culture supernatants and are referred to as conditioned media (CM). Among the therapeutically valuable activities obtained, irreversible anti-tumor proliferating activities have been confirmed to be present in useful concentrations which can consistently demonstrate more than 80% growth inhibition against tumor cell lines in a dose-dependent fashion. Compositions having therapeutically valuable biological activities can be obtained from dialyzed and lyophilized conditioned media compositions.

In a first aspect, this invention provides a method for preparing a conditioned media composition having immunosuppressive or non-reversible anti-tumor activity comprising the steps of:

(1) providing pieces of tissue comprising immune cells from an elasmobranch fish, (2) culturing and incubating the pieces of tissue in a cell culture medium under serum-free conditions, and (3) removing cells from the cell culture medium comprising the cultured and incubated pieces of tissue to produce a cell-free supernatant comprising molecules produced by the immune cells, wherein the cell culture medium has osmolarity of 800–1200 mOsm and comprises urea and a salt and does not comprise trimethylamine N-oxide.

In a second aspect, this invention provides a conditioned media composition having immunosuppressive or non-reversible anti-tumor activity, wherein the conditioned media composition is prepared by a method comprising the steps of:

(1) providing pieces of tissue comprising immune cells from an elasmobranch fish, (2) providing a cell culture medium having osmolarity of 800–1200 mOsm and comprising urea and a salt and not comprising trimethylamine N-oxide, (3) culturing and incubating the pieces of tissue in the cell culture medium under serum-free conditions, and (4) removing cells from the cell culture medium containing the cultured and incubated pieces of tissue to produce a cell-free supernatant comprising molecules produced by the immune cells.

In a third aspect, this invention provides a method for preparing a conditioned media composition having immunosuppressive or anti-tumor activity comprising the steps of:

(1) providing pieces of tissue comprising immune cells from a shark of order Carcharhiniformes, (2) culturing and incubating the pieces of tissue in a cell culture medium under serum-free conditions, and (3) removing cells from the cell culture medium comprising the cultured and incubated pieces of tissue to produce a cell-free supernatant comprising molecules produced by the immune cells, wherein the cell culture medium has osmolarity of 800–1200 mOsm and comprises urea and a salt.

In a fourth aspect, this invention provides a conditioned media composition having immunosuppressive or anti-tumor activity, wherein the conditioned media composition is prepared by a method comprising the steps of:

(1) providing pieces of tissue comprising immune cells from a shark of order Carcharhiniformes, (2) providing a cell culture medium having osmolarity of 800–1200 mOsm and comprising urea and a salt, (3) culturing and incubating the pieces of tissue in the cell culture medium under serum-free conditions, and (4) removing cells from the cell culture medium containing the cultured and incubated pieces of tissue to produce a cell-free supernatant comprising molecules produced by the immune cells.

BRIEF DESCRIPTION OF THE DRAWINGS

The present invention will be readily understood by way of the specific embodiments shown in the appended figures, the purpose of which is to illustrate the invention rather than to limit its scope.

DETAILED DESCRIPTION OF THE INVENTION

Figure 1:
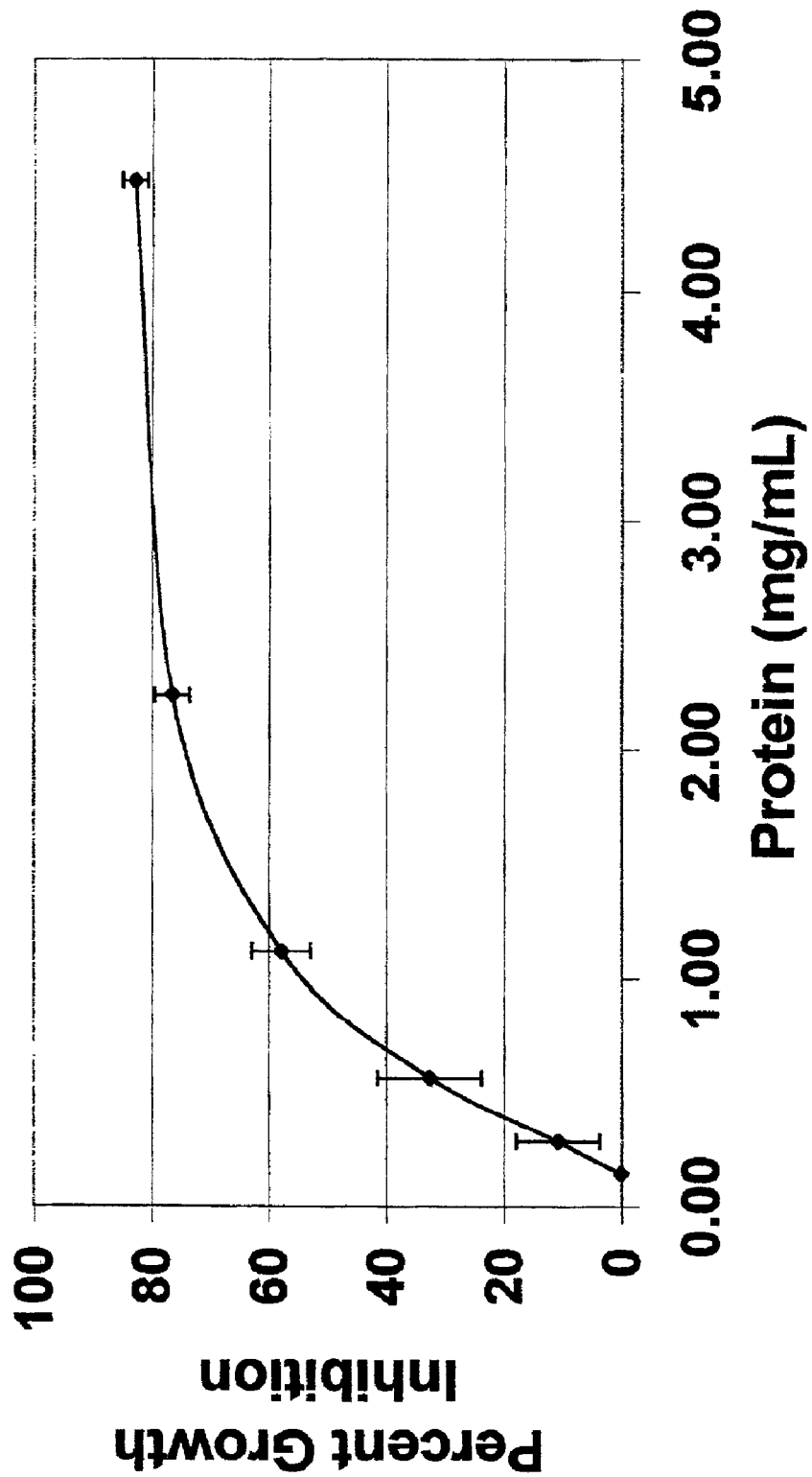
FIG. 1 shows a dose-response growth inhibitory activity of bonnethead shark epigonal conditioned media prepared according to the invention on A375.S2 cell line.

The foregoing detailed description of the invention includes passages which are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions thereof relate to specific embodiments of the invention, it is to be understood that where a specific feature is disclosed in the context of a particular figure, such feature can also be used, to the extent appropriate, in the context of another figure, in combination with another feature, or in the invention in general.

The immune cells used in the present invention come from elasmobranch fishes, including sharks, rays and skates. It is preferred that the immune cells come from tissue from the Leydig or epigonal organ of elasmobranch fishes. It is especially preferred that the immune cells come from tissue from the epigonal or Leydig organ of a shark of order Carcharhiniformes or of order Orectolobiformes. It is particularly preferred that the immune cells come from tissue from the epigonal or Leydig organ of a shark in the family Carcharhinidae (e.g., lemon, bull, blacknose, blacktip, tiger, and sandbar sharks) or in the family Sphymidae (e.g., bonnethead, hammerhead, and scalloped hammerhead) or in the family Ginglymostomatidae (e.g., nurse shark). If a shark in the family Ginglymostomatidae is used, it is preferred that the shark have overall length longer than 75 cm. It is most especially preferred that the immune cells come from tissue from the epigonal organ of a bonnethead shark (*Sphyrna tiburo*) or lemon shark (*Negaprion brevirostris*). The elasmobranch fishes which supply the immune cells for this invention may be either male or female.

It is preferred that the elasmobranch used as the source of immune cells be healthy and that the tissue be collected under aseptic conditions. For making the conditioned media (CM) described herein, it is preferred that the tissue be used fresh, immediately following excision from the animal, as soon as possible following excision from the animal, preferably not to exceed 24 h. It is preferred that tissue from neighboring organs be carefully removed by dissection. For example, if an epigonal organ is to be used as the source of immune cells, then it is preferred that any gonadal tissue be excised and discarded. In addition, it is preferred that the tissue be rinsed with sterile elasmobranch-modified phosphate buffered saline solution (E-PBS) to remove any external blood or other body fluids. For example, the E-PBS used can comprise NaCl and $NaH_2PO_4$ which has been pH adjusted to 7.2–7.4 and has been filter sterilized. Small pieces of the tissue being used as the source of the immune cells should be provided, e.g., the tissue can be minced intopieces smaller than 5 mm² under sterile conditions. Unless it is processed immediately, the tissue should be kept cold (e.g., 4° C.) after dissection and before mincing.

One aspect of the present invention describes a conditioned media composition made from elasmobranch immune cells having therapeutically valuable biologically active components (e.g., irreversible antitumor activity or immunosuppressive activity) using a cell culture medium which has been modified to approximate the normal osmolarity of elasmobranch cells, but does not contain TMAO, and a method of preparation thereof. It is preferred that the osmolarity of the cell culture medium be 800–1200 mOsm, particularly 900–1100 mOsm, especially 950–1000 mOsm, most especially 970 mOsm. The osmolarity of the cell culture medium can be adjusted using urea and salt. It is preferred that the salt used be sodium chloride. In addition, antibiotics (e.g., penicillin, streptomycin sulfate, neomycin, and Amphotericin B) and DNAse (deoxyribonuclease) can be added to the modified cell culture medium. Conditioned media compositions from shark epigonal organs as described herein demonstrate consistent anti-tumor activity at high levels (e.g., greater than 70%, or greater than 80%). Finally the pH of the modified cell culture medium can be adjusted to near neutral pH, e.g., 7.0–7.4. It is preferred that the modified cell culture medium be filter sterilized before use.

The present invention also describes a conditioned media composition made from immune cells from tissue from the epigonal or Leydig organ of a shark of order Carcharhiniformes having therapeutically valuable biologically active components (e.g., irreversible anti-tumor activity or immunosuppressive activity) using a cell culture medium which has been modified to approximate the normal osmolarity of elasmobranch cells, and a method of preparation thereof. It is especially preferred that the sharks be in the family Carcharhinidae (e.g., lemon, bull, blacknose, blacktip, tiger, or sandbar sharks) or in the family Sphymidae (e.g., bonnethead, hammerhead, or scalloped hammerhead sharks). It is most especially preferred that the immune cells come from tissue from the epigonal organ of a bonnethead shark (*Sphyrna tiburo*) or lemon shark (*Negaprion brevirostris*). It is preferred that the osmolarity of the cell culture medium be 800–1200 mOsm, particularly 900–1100 mOsm, especially 950–1000 mOsm, most especially 970 mOsm. The osmolarity of the cell culture medium can be adjusted using urea and salt (e.g., NaCl). In addition, antibiotics (e.g., penicillin, streptomycin sulfate, neomycin, and Amphotericin B) and DNAse can be added to the modified cell culture medium. The pH of the modified cell culture medium can be adjusted to near neutral pH, e.g., 7.0–7.4. It is preferred that the modified cell culture medium be filter sterilized before use.

The small pieces of tissue comprising immune cells from the elasmobranch fishes are incubated in the modified cell culture medium under serum-free conditions for two to four days). It is preferred that the incubation be carried out between 20–29° C., under 4–10% $CO_2$ for 1–7 days. It is especially preferred that the incubation be carried out at 25° C., under 5% $CO_2$ for 2–4 days. After incubation, a cell-free conditioned media can be prepared, preferably by centrifugation, although any suitable technique may be used (e.g., filtration). The cell-free conditioned media can be further processed by dialysis against a buffer solution or water, lyophilization, and reconstitution in a mammalian tissue culture medium or other buffer. Alternatively, if it is not desired to process the conditioned media directly after its preparation, the conditioned media can be prepared through step 3) of the first and third aspect of the invention or step 4) of the second and fourth aspects of the invention, and subsequently stored under cold conditions, preferably below 0° C. (e.g., −20° C. or −80° C.), for as long as desired, and then restored to room temperature and dialyzed against a buffer solution or water and lyophilized and reconstituted in mammalian tissue culture media or other buffer. The lyophilized samples can be stored frozen, (e.g., −20° C. to −80° C.), preferably −80° C. until use in assays. Preferably dialysis is carried out with dialysis tubing having 6000–8000 Da molecular weight cut off (hereinafter, MWCO), but MWCO ranging from 1000 Da–100 kDa may also be used.

The cells removed from the conditioned media can be placed into culture for a second harvest while maintaining sterile conditions. Fresh cell culture media (modified according to the method described herein) should be use to re-culture the cells. The cells should be reincubated according to the method described herein.

Figure 2:
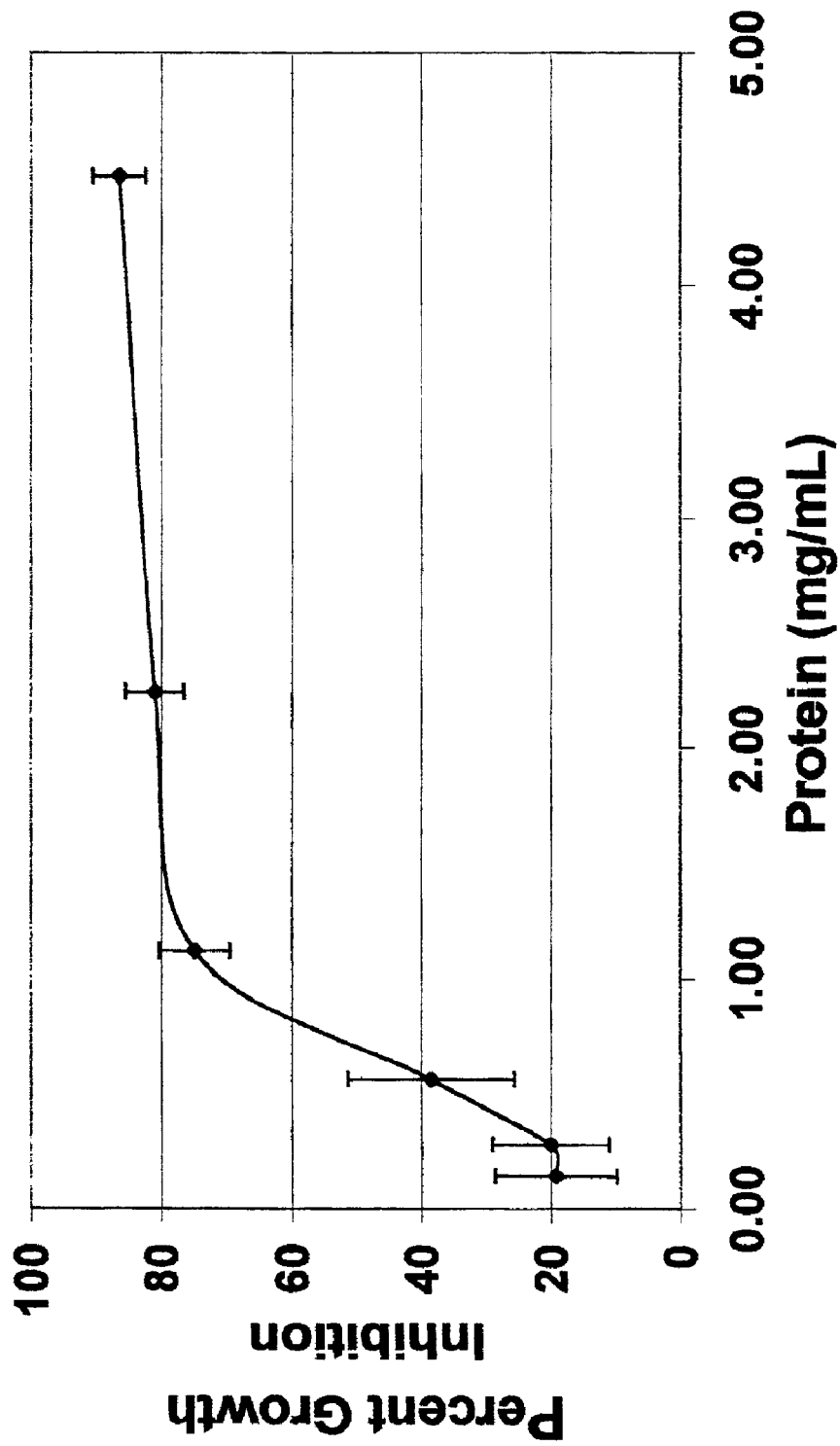
FIG. 2 shows a dose-response growth inhibitory activity of bonnethead shark epigonal conditioned media prepared according to the invention on WEHI 164 cell line.
Figure 3:
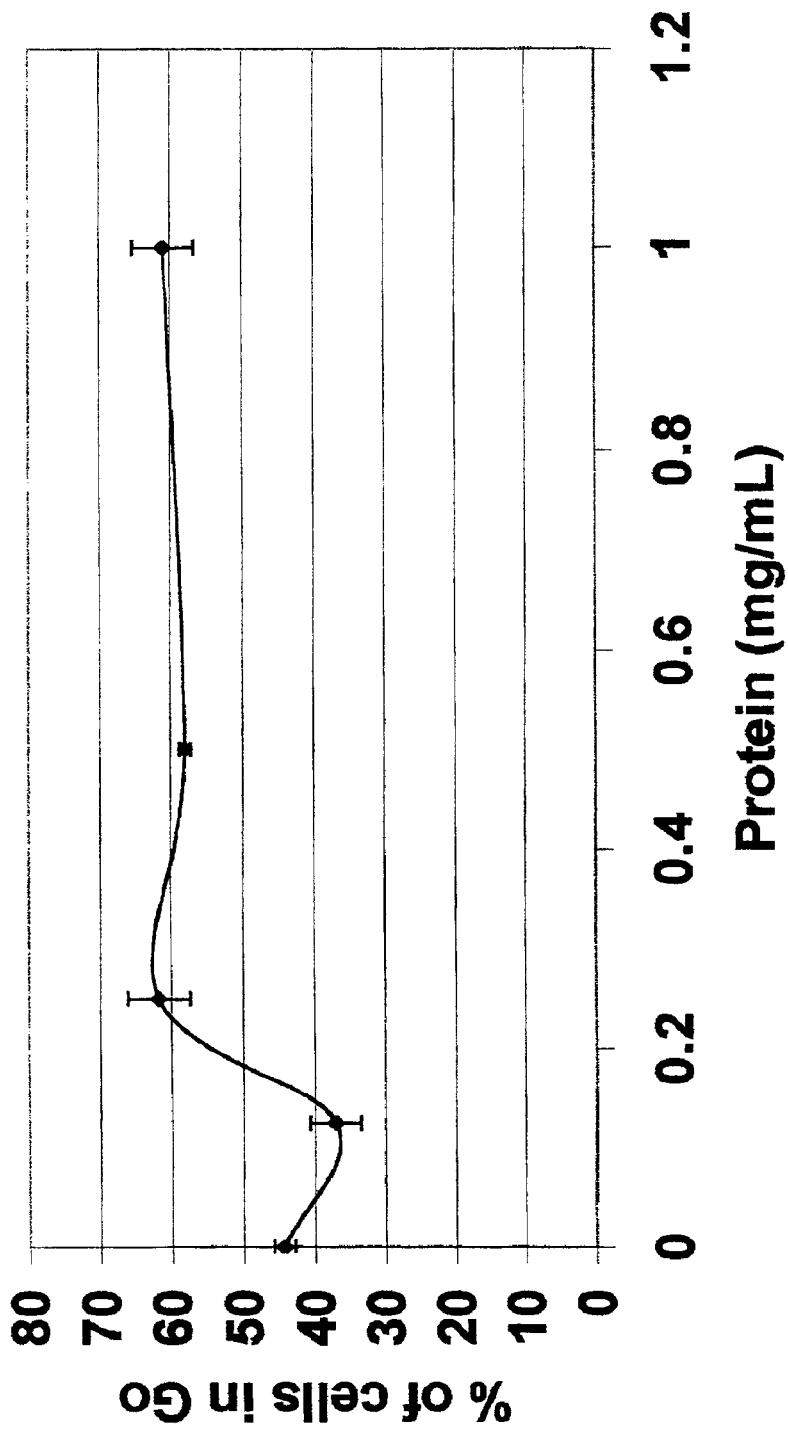
FIG. 3 shows the effect of bonnethead epigonal conditioned media preparations according to the invention on the Go phase of the cell cycle in Daudi cell line.
Figure 4:
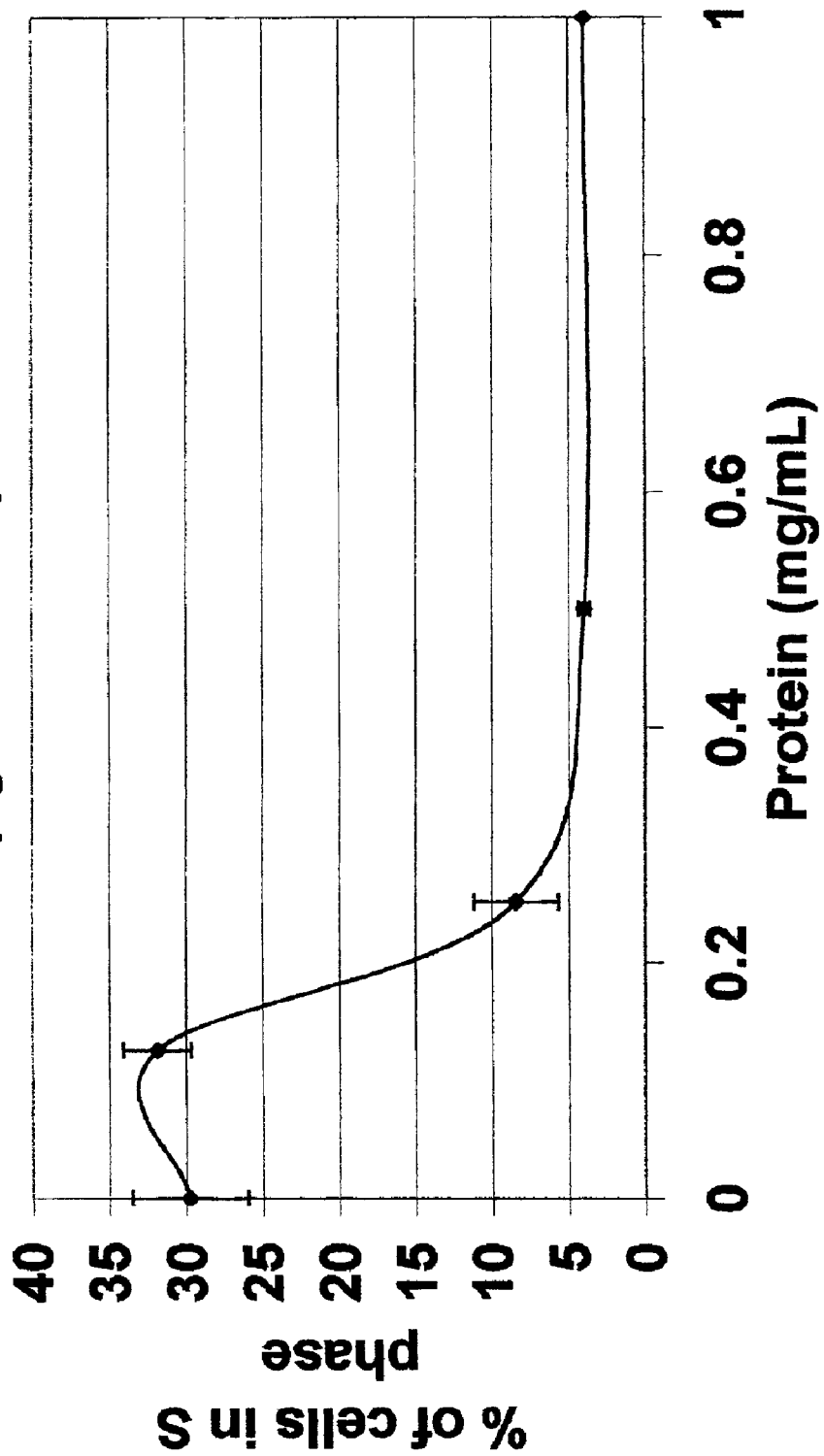
FIG. 4 shows the effect of bonnethead epigonal conditioned media preparations according to the invention of the S phase of the cell cycle in Daudi cell line.
Figure 5:
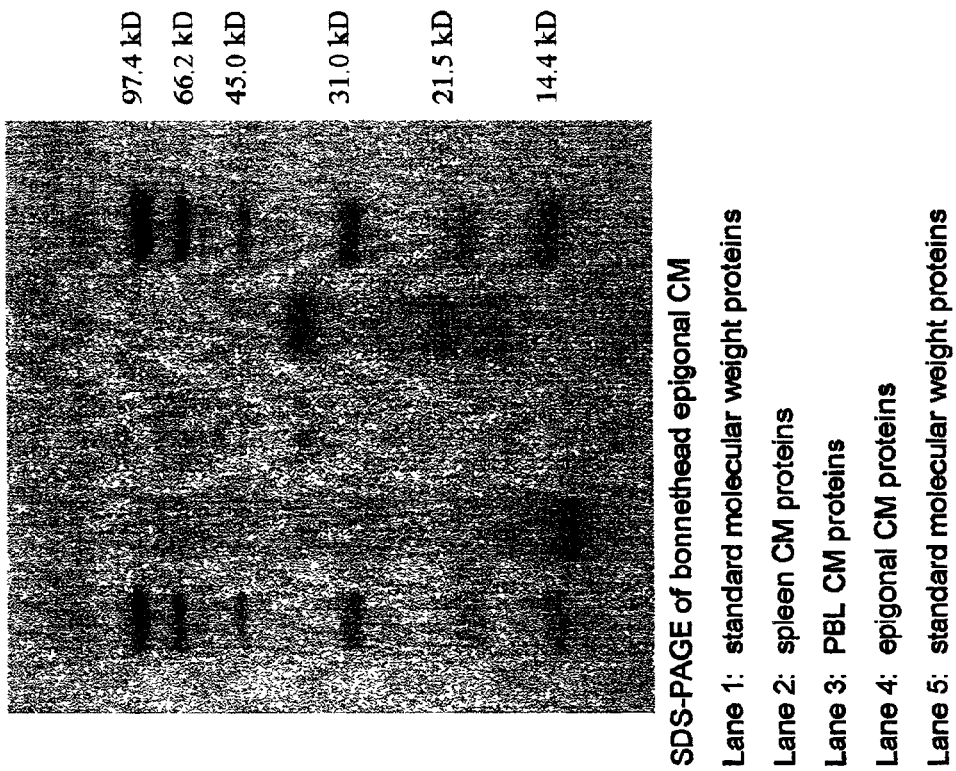
FIG. 5 shows the electrophoretic profile on SDS-PAGE of bonnethead epigonal conditioned media according to the invention. Lane 1: Standard molecular weight proteins; Lane 2: Spleen CM proteins which show no tumor inhibitory activity; Lane 3: Peripheral blood leukocytes (PBL) CM proteins which show no tumor inhibitory activity; Lane 4: Epigonal CM proteins from cultured media preparations according to the invention; Lane 5: Standard molecular weight proteins.
Figure 6:
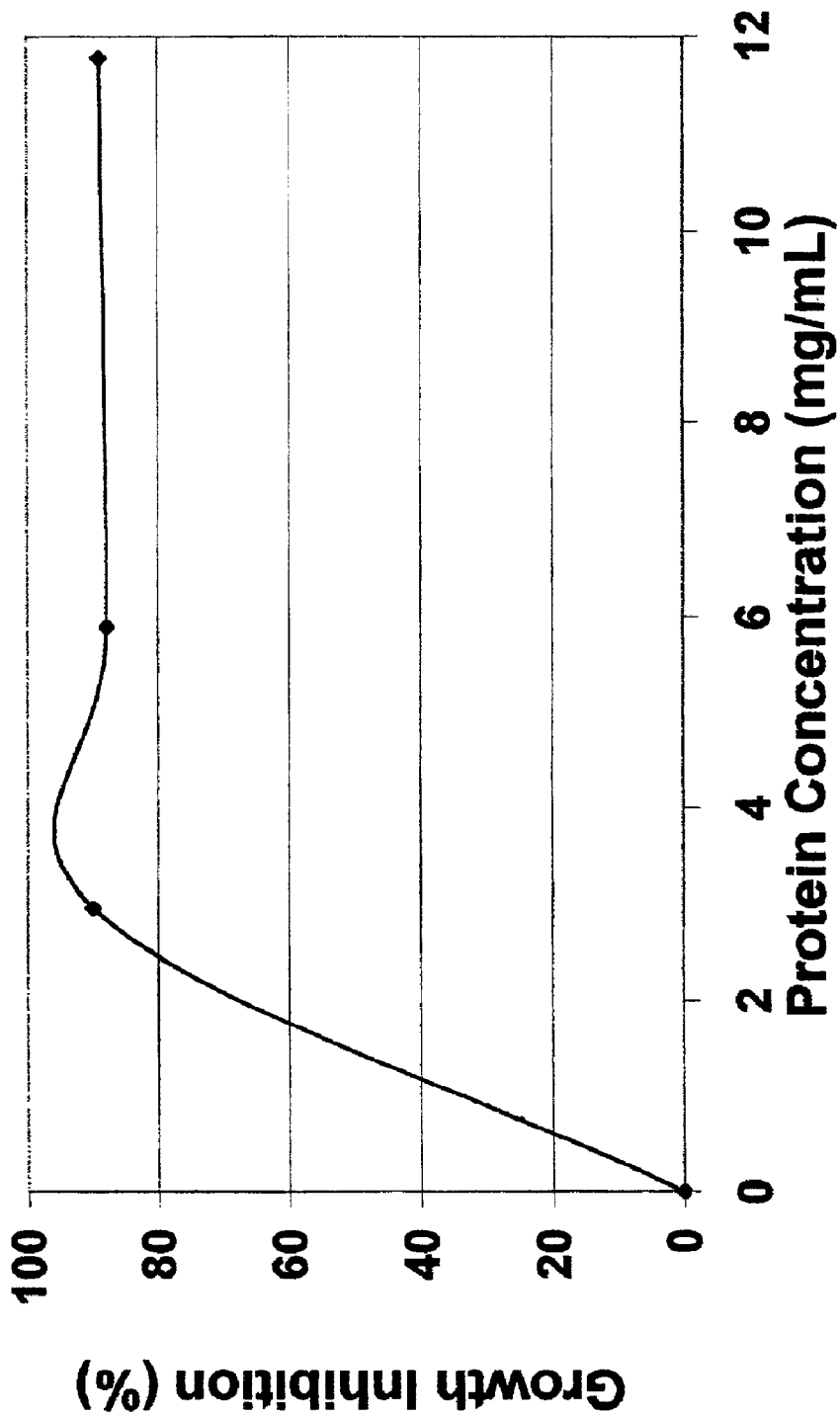
FIG. 6 shows dose-response growth inhibitory activity of lemon shark epigonal CM preparations according to the invention on A375.S2 cell line.
Figure 7:
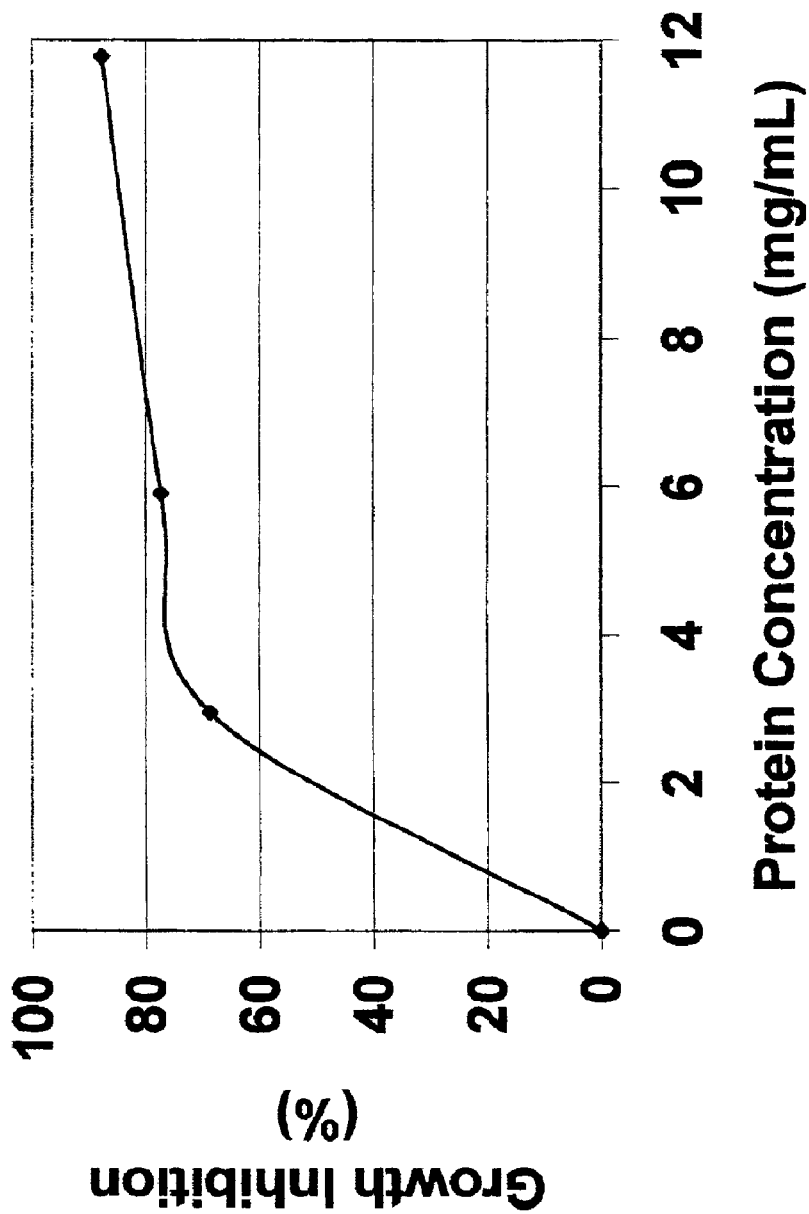
FIG. 7 shows dose-response inhibitory activity of lemon shark epigonal CM preparations on WEHI 164 cell line.

The cell-free conditioned media compositions described herein have been tested for anti-tumor activity on tumor cell lines A375.S2 [human malignant melanoma, American Type Culture Collection (ATCC) number CRL-1872, WEHI 164 (mouse fibrosarcoma, ATCC number CRL-1751), and Daudi (human Burkitt's lymphoma, ATCC number CCL 213)]. The invention is illustrated by the following drawings in which FIGS. 1 and 2 show that conditioned media prepared using tissue from an epigonal organ of a bonnethead shark using the method described herein is effective in inhibiting growth of more than 80% of the A375.S2 cells and WEHI 164 cells in culture, respectively. FIG. 3 shows that the percentage of Daudi cells remaining in the Go phase of the cell cycle are increased by approximately 35% (33–37%) when treated with conditioned media prepared using tissue from an epigonal organ of a bonnethead shark using the method described herein. FIG. 4 shows that the percentage of Daudi cells entering the S phase of the cell cycle, when treated with epigonal conditioned media, is 85% less than the percentage of untreated Daudi cells entering the S phase of the cell cycle. Conditioned media prepared using tissue from epigonal organs of bonnethead shark inhibit cell division in tumor cells. Conditioned media compositions prepared from the spleen or peripheral blood leukocytes from the same animal demonstrate no tumor inhibitory activity (FIG. 5). FIGS. 6 and 7 show that conditioned media prepared using tissue from an epigonal organ of a lemon shark using the method described herein is effective in inhibiting growth of more than 85% of A375.S2 cells and more than 80% effective in inhibiting growth of WEHI 164 cells. All anti-tumor activity demonstrated by the conditioned media compositions described herein is non-reversible, i.e., if the anti-tumor composition described herein is removed from the cell tumor lines and the lines are washed, tumor cell growth does not resume.

The molecules or molecular aggregates isolated from the conditioned media described herein comprise a protein or proteins having molecular weights or aggregate molecular weights ranging from 6000 Da to greater than 100 kDa. The proteins may comprise subunits having molecular weight less than 100 kDa. Ultrafiltration using a membrane having a molecular weight cutoff can be used to concentrate the liquid preparations described herein. Preferably the MWCO is 3 kDa–30 kDa, and more preferably the MWCO is about 10 kDa. The molecules or molecular aggregates isolated from conditioned media obtained from epigonal organs of lemon shark and bonnethead shark are partially heat labile at 56° C. and completely heat labile above 75° C.

The present invention includes therapeutic compositions comprising as an active ingredient an effective amount (e.g., final concentration of more than 0.25 mg/ml) of the conditioned media compositions described herein, and therapeutic methods comprising the use of the conditioned media compositions described herein. Therapeutic compositions and methods developed utilizing conditioned media compositions described herein include anti-tumor treatments (i.e., cancer) and immunosuppressive therapy (e.g., in transplants). For example, irreversible anti-tumor activity has been demonstrated against human malignant melanoma and mouse fibrosarcoma.

EXAMPLES

Example 1

Bonnethead sharks (*Sphyrna tiburo*) are a common shark species found off the Gulf coast of Florida, USA. The sharks used in this Example were caught in nets and transported live to Mote Marine Laboratory. Sharks were maintained in flow-through tanks at Mote Marine Laboratory for short periods of time. Mature animals, both male and female, were used in this Example. Epigonal tissue was collected from healthy bonnethead sharks. The epigonal tissue was collected under aseptic conditions. The tissue was carefully rinsed with sterile elasmobranch-modified phosphate buffered saline (E-PBS) to remove any external blood or other body fluids. The tissue was used fresh, immediately following excision from the animal. The tissue was kept cold at 4° C. for 10–15 minutes until dissection was complete before culturing. The E-PBS used was 0.45 M NaCl, 0.01 M $NaH_2PO_4$ and was pH adjusted to 7.2–7.4 by titrating with 1 N HCl. The E-PBS was filter sterilized through 0.2 μm filter before use. Any gonadal tissue remaining with the epigonal tissue was removed by careful dissection using sterile dissection tools. The epigonal tissue was minced into small (2–5 $mm^2$) pieces with sterile scissors and forceps. The pieces were placed into 75 $mm^2$ sterile tissue culture flasks with elasmobranch-modified RPMI (E-RPMI; 20–40 mL, depending on size of tissue). A small volume was preferred since it was more convenient to manipulate. E-RPMI used in this example was 1.04 g of the cell culture medium RPMI without phenol red (available from Sigma as R8755) dissolved in 80 mL $dH_2O$. The osmolarity of the cell culture medium was adjusted to 970 mOsm by adding 2.16 g urea and 1.11 g NaCl, resulting in final concentrations of 360 mM urea and 188 mM NaCl. Antibiotics were added at final concentrations of 50 U penicillin G, 50 μg streptomycin sulfate, 0.1 mg neomycin/mL (available from Sigma as P3364). Amphotericin B was added at a final concentration of 0.25 μg/mL. Sodium bicarbonate was added and the pH was adjusted to 7.2–7.4. The volume was brought to 100 mL with $dH_2O$. E-RPMI was filter sterilized through a 0.2 μm filter before use. The cultures were incubated at 25° C. in 5% $CO_2$ for 2–4 days, with the length of time within this range not significantly altering the resultant activity. Conditioned media was harvested by removing cells with centrifugation at 20,000×g for 25 minutes at 4° C. This was repeated twice. To test this preparation against mammalian tumor cell lines, it was necessary to remove the salts and urea that comprise elasmobranch culture conditions. The conditioned media compositions were dialyzed against 50 mM ammonium bicarbonate at pH 7.4 at 4° C., and changed daily for 4 days. If it was not possible to dialyze immediately, the conditioned media compositions were frozen at –20° C. or –80° C. for unspecified lengths of time before dialysis with no loss in measurable biological activity. Dialysis was accomplished under cold conditions using dialysis tubing with 6000–8000 Da molecular weight cut-off and continual stirring. If precipitate was present in the tubing after dialysis was complete, the sample was briefly centrifuged at 20,000×g to remove precipitate. The dialyzed sample was frozen at –80° C. and then lyophilized until complete (typically 48 hours). Lyophilized samples were stored at –80° C. until use in assays. Protein concentration was determined by Bradford method on all samples before using in assays. After initial harvesting of conditioned media, once-cultured and incubated epigonal cells were placed into culture for a second incubation maintaining sterile conditions. Fresh E-RPMI was used for the second culture, and the cells were incubated for an additional 2 days. The second harvest of conditioned media had activity equivalent to the initial harvest. Lyophilized samples were resuspended in mammalian cell culture media before biological activity assays were conducted. Reconstituted samples were filtered through 0.2 μm sterile filters before use. Ultrafiltration using a membrane having a molecular weight cut-off value of about 30 kDa can be used to concentrate the liquid preparations described herein.

In vitro assays were conducted on the cancer cell lines A375.S2 (human malignant melanoma, American Type Culture Collection ATCC number CRL-1872), WEHI 164 (mouse fibrosarcoma, ATCC number CRL1751) and Daudi (human Burkitt's lymphoma, ATCC number CCL 213).

For A375.S2 cells, a cell culture medium having 0.97 g Minimum Essential Medium Eagle (available from Sigma as M0643) was dissolved in approximately 80 mL $dH_2O$. Antibiotics were added to a final concentration of 50 U penicillin G, 50 μg streptomycin sulfate, 0.1 mg neomycin/mL medium (available from Sigma as P3364). Amphotericin B was added at final concentrations of 0.25 μg/mL (Sigma A9528). Sodium bicarbonate was added and pH adjusted to 7.2–7.4. The medium was made to 90 mL with $dH_2O$, filter sterilized through 0.2 μm filter, and supplemented with 10% (by volume) fetal bovine serum (FBS) to make 100 mL final volume. Serum (available from Hyclone) was heat-inactivated at 56° C. for 30 minutes before use. Serum was aliquoted in sterile tubes and stored at –20° C. This solution was prepared fresh weekly and stored at 4° C.

For WEHI 164 cells, a cell culture medium having 1.04 g RPMI without phenol red was dissolved in approximately 80 mL $dH_2O$. Antibiotics were added at final concentrations of 50 U penicillin G, 50 μg streptomycin sulfate, 0.1 mg neomycin/mL medium (Sigma P3364). Amphotericin B was added to a final concentration of 0.25 μg/mL. Sodium bicarbonate was added and pH adjusted to 7.2–7.4. The volume of the medium was adjusted to 90 mL with $dH_2O$, filter sterilized with 0.2 μm filter, and 10% (by volume) heat inactivated FBS was added for a final volume of 100 mL. This solution was prepared fresh weekly and stored at 4° C.

For Daudi cells, a cell culture medium having 1.04 g RPMI without phenol red was dissolved in approximately 80 mL with $dH_2O$ for 100 mL of medium (final volume). These cells were cultured without antibiotics. Sodium bicarbonate was added and pH adjusted to 7.2–7.4. RPMI was filter sterilized through 0.2 μm filter before use. This solution was prepared fresh weekly and stored at 4° C. Heat-inactivated FBS (available from Hyclone) was added before use at 20% (by volume).

Once A375.S2 and WEHI 164 cells reached confluence, they were harvested by standard procedures and concentration-adjusted to 5×10$^4$ cells/mL and 100 μL cell suspension was added per well of 96 well microtiter plate. Cells were grown in the presence or absence of different concentrations of reconstituted lyophilized samples as prepared above. The lyophilized conditioned media composition was thereby resuspended in culture medium and sterile filtered so that water soluble components were recovered and tested. All experiments were performed in at least triplicate. Cells were then grown in an incubator under a constantly humidified atmosphere containing 5% $CO_2$ at 37° C. for 3 days. Conditioned media was added in dilutions of 1:2, 1:4, 1:8, 1:16 and 1:32, corresponding to protein concentrations ranging from 4.5 mg/mL to 0.1 mg/mL final concentration. Cell growth inhibition was measured by the MTT (3-(4,5-dimethylthizaole-2-yl) 2,5-diphenyltetrazolium bromide) assay (available from Sigma as M2128) following 3 days of culture.

Daudi cells were distributed into 96 well microtiter plates. Cells were grown in the presence or absence of different concentrations of conditioned media prepared from the epigonal cells. Reconstituted lyophilized samples were prepared as described above. Conditioned media was added at concentrations of 0.125 to 1 mg/mL. The percentages of tumor cell growth inhibition presented in FIGS. 1 and 2 show that the conditioned media compositions described herein can inhibit in a dose-dependent manner the growth of the cells of the A375.S2 and WEHI 164 tumor cell lines. Doses of 2.2 and 4.5 mg/mL of the conditioned media inhibit growth at greater than 80% after three days of treatment, as shown in FIG. 1. A dosage of 1.1 mg/mL inhibits growth of WEHI 164 cells nearly 80%, whereas doses of 2.2 and 4.5 mg/mL inhibit growth of WEHI cells greater than 80%. In FIGS. 3 and 4, the effects of conditioned media on the Daudi cell cycle are shown. In Daudi cells, 250 μg/mL of the conditioned media potently inhibited DNA synthesis (S-phase) of Daudi cells by arresting cells in $G_o$ with little increase in apoptosis, as measured at 36 hours following exposure.

The average protein concentration of the conditioned media prepared in this Example was 9.16+/-0.63 mg/mL, with a sample size of 21. The protein content of the conditioned media was analyzed by Bradford method. SDS polyacrylamide gel electrophoresis (SDS-PAGE) was performed to characterize the molecular weights of the protein components. FIG. 5 shows that the conditioned media prepared from epigonal tissue from a bonnethead shark contains three major protein bands have molecular weights of approximately 43 kDa, 21 kDa, and 17 kDa.

The conditioned media prepared in this Example demonstrated anti-proliferative activity on all tumor cell lines tested. The strongest inhibitions of greater than 80% were obtained with final concentrations of 1–4.5 mg/mL of the conditioned media on human malignant melanoma cells (A375.S2) and mouse fibrosarcoma cells (WEHI 164). For cells of human Burkitt's lymphoma, the strongest inhibition of growth cells was observed with a dosage of 250 μg/mL of the reconstituted lyophilized conditioned media.

Example 2

Lemon sharks (*Negaprion brevirostris*) were caught off the Gulf Coast of Florida using hook and line. Epigonal tissue was obtained from fresh specimens and conditioned media were prepared as in Example 1. The conditioned media showed anti-proliferative activity on all tumor cell lines tested (A375.S2 and WEHI 164) and the effects of growth inhibition on dose are shown in FIGS. 6 and 7. Growth inhibition of WEHI 164 cells of >90% was achieved using a dose of approximately 3 mg/mL.

Example 3

Nurse sharks and cleamose skates were obtained from tanks maintained at Mote Marine Laboratory in Sarasota, Fla. Epigonal tissue was obtained from fresh specimens of nurse sharks and epigonal and Leydig organ tissues were obtained from fresh specimens from cleamose skates. Conditioned media were prepared as in Example 1. These preparations were evaluated for anti-tumor activity in various mammalian tumor cell lines. Inconsistent anti-tumor activity resulted from those preparations from nurse shark and cleamose skate immune tissue and they inhibited growth of less than 40% of A375.S2 cells and 50–70% of WEHI 164 cells.

It will be understood that the above-described compositions and methods are merely illustrative of applications of the principles of this invention and many other embodiments and modifications may be made without departing from the spirit and scope of the invention as defined in the claims.

What is claimed is:

1. A method for preparing a conditioned media composition having irreversible anti-tumor activity comprising the steps of:
   (1) providing pieces of tissue comprising minced epigonal organ or minced Leydig organ from shark from the order Carcharhiniformes or order Orectolobiformes,
   (2) culturing and incubating the pieces of tissue in a cell culture medium under serum-free conditions, and
   (3) removing cells from the cell culture medium comprising the cultured and incubated pieces of tissue to produce a cell-free supernatant,
   wherein the cell culture medium has osmolarity of 800–1200 mOsm and comprises urea and a salt and does not comprise trimethylamine N-oxide.

2. A method as in claim 1 wherein the shark is in the family Carcharhinidae or in the family Sphyrnidae.

3. A method as in claim 2 wherein the shark is a bonnethead shark or a lemon shark.

4. A method as in claim 1 wherein the cell culture medium further comprises an antibiotic.

5. A method as in claim 1 wherein a centrifuging process is used to remove cells from the cell culture medium comprising the cultured and incubated pieces of tissue to produce a cell-free supernatant.

6. A method as in claim 1 further comprising the steps of:
   (4) dialyzing the cell-free supernatant against water or a buffer solution to form a dialyzed supernatant, and
   (5) lyophilizing the dialyzed supernatant, and
   (6) reconstituting in a buffer.

7. A method as in claim 6 further comprising the step of storing the cell-free supernatant at a temperature of 0° C. or lower before the step of dialyzing the cell-free supernatant against water or a buffer solution.

8. A conditioned media composition having irreversible anti-tumor activity, wherein the conditioned media composition is prepared by a method comprising:
   (1) providing pieces of tissue comprising minced epigonal organ or minced Leydig organ from shark from the order Carcharhiniformes or order Orectolobiformes,
   (2) providing a cell culture medium having an osmolarity of 800–1200 mOsm and comprising urea and a salt and not comprising trimethylamine N-oxide,
   (3) culturing and incubating the pieces of tissue in the cell culture medium under serum-free conditions, and
   (4) removing the cells from the cell culture medium comprising the cultured and incubated pieces of tissue to produce a cell-free supernatant.

9. A conditioned media composition as in claim 8, wherein the cell-free supernatant is dialyzed, lyophilized and reconstituted in a buffer.

10. A conditioned media composition as in claim 8, wherein the supernatant comprises protein molecules.

11. A conditioned media composition as in claim 10, wherein the protein molecules have molecular weights less than 100 kDa.

12. A conditioned media composition as in claim 8, wherein the supernatant is heat labile above 75° C.

13. A conditioned media composition as in claim 9, wherein the cell-free supernatant is stored at a temperature at or below 0° C. before being dialyzed, lyophilized and reconstituted in a buffer.

14. A conditioned media composition as in claim 8, wherein the shark is in the family Carcharhinidae or in the family Sphyrnidae.

15. A conditioned media composition as in claim 14, wherein the shark is a bonnethead shark or a lemon shark.

16. A method for inhibiting tumor cell growth comprising exposing tumor cells to the composition according to claim 8.

17. A method of claim 16, wherein the tumor cells are human malignant melanoma, mouse fibrosarcoma or human Burkitt's lymphoma.

18. A method for preparing a conditioned media composition having irreversible anti-tumor activity comprising the steps of:
   (1) providing pieces of tissue comprising epigonal organ or Leydig organ from shark from the order Carcharhiniformes,
   (2) culturing and incubating the pieces of tissue in a cell culture medium under serum-free conditions, and
   (3) removing cells from the cell culture medium comprising the cultured and incubated pieces of tissue to produce a cell-free supernatant,
wherein the cell culture medium has osmolarity of 800–1200 mOsm and comprises urea, a salt and an antibiotic.

19. A method as in claim 18 wherein the shark is in the family Carcharhinidae or in the family Sphyrnidae.

20. A method as in claim 19 wherein the shark is a bonnethead shark or a lemon shark.

21. A method as in claim 18 wherein a centrifuging process is used to remove cells from the cell culture medium comprising the cultured and incubated pieces of tissue to produce a cell-free supernatant.

22. A method as in claim 18 further comprising the steps of:
   (4) dialyzing the cell-free supernatant against water or a buffer solution to form a dialyzed supernatant, and
   (5) lyophilizing the dialyzed supernatant, and
   (6) reconstituting in a buffer.

23. A method as in claim 22 further comprising the step of storing the cell-free supernatant at a temperature of 0° C. or lower before the step of dialyzing the cell-free supernatant against water or a buffer solution.

24. A conditioned media composition having irreversible anti-tumor activity, wherein the conditioned media composition is prepared by a method comprising:
   (1) providing pieces of tissue comprising epigonal organ or Leydig organ from shark from the order Carcharhiniformes,
   (2) providing a cell culture medium having an osmolarity of 800–1200 mOsm and comprising urea and a salt and an antibiotic,
   (3) culturing and incubating the pieces of tissue in a cell culture medium under serum-free conditions, and
   (4) removing cells from the cell culture medium comprising the cultured and incubated pieces of tissue to produce a cell-free supernatant.

25. A conditioned media composition as in claim 24, wherein the cell-free supernatant is dialyzed, lyophilized and reconstituted in a buffer.

26. A conditioned media composition as in claim 24, wherein the shark is in the family Carcharhinidae or in the family Sphyrnidae.

27. A conditioned media composition as in claim 26, wherein the shark is a bonnethead shark or a lemon shark.

28. A conditioned media composition as in claim 24, wherein the supernatant comprises protein molecules.

29. A conditioned media composition as in claim 28, wherein the protein molecules have molecular weights less than 100 kDa.

30. A conditioned media composition as in claim 24, wherein the supernatant is heat labile above 75° C.

31. A conditioned media composition as in claim 25, comprising the supernatant stored at a temperature at or below 0° C. before being dialyzed, lyophilized and reconstituted in a buffer.

* * * * *